US011369587B2

(12) United States Patent
Zhong et al.

(10) Patent No.: US 11,369,587 B2
(45) Date of Patent: *Jun. 28, 2022

(54) INJECTABLE PHARMACEUTICAL COMPOSITION OF TECOVIRIMAT AND PREPARATION METHOD THEREOF

(71) Applicant: Institute of Pharmacology and Toxicology Academy of Military Medical Sciences P.L.A. China, Beijing (CN)

(72) Inventors: Wu Zhong, Beijing (CN); Meiyan Yang, Beijing (CN); Wei Gong, Beijing (CN); Yuli Wang, Beijing (CN); Chunsheng Gao, Beijing (CN); Xinbo Zhou, Beijing (CN); Song Li, Beijing (CN)

(73) Assignee: Institute of Pharmacology and Toxicology Academy of Military Medical Sciences PLA China, Beijing (CN)

( * ) Notice: Subject to any disclaimer, the term of this patent is extended or adjusted under 35 U.S.C. 154(b) by 180 days.

This patent is subject to a terminal disclaimer.

(21) Appl. No.: 16/318,044

(22) PCT Filed: Jul. 4, 2017

(86) PCT No.: PCT/CN2017/091650
§ 371 (c)(1),
(2) Date: Jan. 15, 2019

(87) PCT Pub. No.: WO2018/010571
PCT Pub. Date: Jan. 18, 2018

(65) Prior Publication Data
US 2019/0336479 A1 Nov. 7, 2019

(30) Foreign Application Priority Data
Jul. 15, 2016 (CN) .......................... 201610559479.1

(51) Int. Cl.
*A61K 31/403* (2006.01)
*A61K 47/40* (2006.01)
*A61K 9/19* (2006.01)
*A61K 47/26* (2006.01)

(52) U.S. Cl.
CPC .............. *A61K 31/403* (2013.01); *A61K 9/19* (2013.01); *A61K 47/26* (2013.01); *A61K 47/40* (2013.01)

(58) Field of Classification Search
CPC ........ A61K 31/403; A61K 9/19; A61K 47/26; A61K 47/40
See application file for complete search history.

(56) References Cited

U.S. PATENT DOCUMENTS

| 8,835,501 B2 * | 9/2014 | Bastin .................... A61K 47/18 514/604 |
| 2009/0082400 A1 * | 3/2009 | Lee ....................... A61K 31/453 514/326 |
| 2014/0011854 A1 * | 1/2014 | Tyavanagimatt ...... A61K 47/10 514/410 |
| 2019/0358203 A1 | 11/2019 | Zhong et al. |

FOREIGN PATENT DOCUMENTS

| CN | 1493292 A | 5/2004 |
| CN | 101062044 A | 10/2007 |
| CN | 101062044 MT | * 10/2007 |
| CN | 101189003 A | 5/2008 |
| CN | 105434345 A | 3/2016 |
| JP | 20085404099 | 11/2008 |
| WO | 2005090380 A1 | 9/2005 |
| WO | 2006120456 A1 | 11/2006 |
| WO | 2009018326 A2 | 2/2009 |
| WO | 2012018810 A1 | 2/2012 |

OTHER PUBLICATIONS

Aloisio in Journal of Pharmaceutical Sciences 105 (2016) 2703-2711 (Year: 2016).*
Basavaraj et al. in Pharmaceutical Development and Technology 11:443-451 (2006) (Year: 2006).*
Aloisio et al. in Journal of Pharmaceutical Sciences 105, 2703-2711 (2016) (Year: 2016).*
Aloisio et al., "Solubility and release modulation effect of sulfamerazine ternary complexes with cyclodextrins and meglumine," J. Parmaceutical and Biomedical Analysis 100, 54-73, 2014.
Basavarag et al., "Bioavailability Enhancement of Poorly Water Soluble and Weakly Acidic New Chemical Entity with 2-Hydroxy Propyl-?-Cyclodextrin: Selection of Meglumine, a Polyhydroxy Base, as a Novel Ternary Component," Pharmaceutical Development and technology 11, 443-51, 2006.
Lee et al., "Preparation and Evaluation of Inclusion Complex of Lansoprazole with 2-HP-?-Cyclodextrin and Meglumine," J. Kor. Pharm. Sci. 34, 269-74, 2004.
Office Action dated May 23, 2019 in Japanese Patent Application No. 2019-501651, 4 pages.
International Search Report for PCT/CN2017/091650, dated Oct. 12, 2017, 3 pages.
Chaudhari & Patil, "Pharmaceutical excipients: a review," Int. J. Adv. Pharm. Biol. Chem. 1, 21-34, 2012.
Chinese Patent Application No. 20160560206.9, first Office Action, dated May 28, 2020.
Chinese Patent Application No. 20160560206.9, first search report, dated May 28, 2020.

(Continued)

*Primary Examiner* — Dennis Heyer
(74) *Attorney, Agent, or Firm* — Banner & Witcoff, Ltd.

(57) ABSTRACT

The present invention relates to a pharmaceutical composition of Tecovirimat for injection, comprising Tecovirimat as an active ingredient, cyclodextrin and an additive. The present invention also relates to a method for preparing the pharmaceutical composition. The composition improves the solubility of Tecovirimat in water by using cyclodextrin and meglumine in combination, as compared with the solubility of Tecovirimat in water by using cyclodextrin or meglumine alone.

19 Claims, 2 Drawing Sheets

(56) References Cited

OTHER PUBLICATIONS

Chinese Patent Application No. 20160560206.9, second Office Action.
Chinese Patent Application No. 20160560206.9, supplemental search report.
Desai & Prabhakar, "Development and evaluation of orally disintegrating tablets of cilostazol-?-cyclodextrin inclusion complexes," Drug Dev. Ind. Pharm. 41, 1589-607, 2015.
Feng-ying et al., "Determination of the equilibrium solubility of tecovirimat and its apparent oil/water partition coefficients using HPLC," Mil. Med. Sci. 36, 49-51, 2012 with translation.
International Preliminary Opinion on Patentability for PCT/CN2017/091648, dated Nov. 10, 2018.
International Search Report for PCT/CN2017/091648, dated Oct. 11, 2017.
Vakani et al., "Influence of auxiliary agents on solubility and dissolution profile of repaglinide with hydroxypropyl-?-cyclodextrin inclusion complex formation and its solid-state characterization," J. Incl. Macrocycl. Chem. 83, 3239-50, 2015.
Zhong et al., U.S. Appl. No. 16/317,942 non-final office action dated Oct. 23, 2020.
Zhong et al., U.S. Appl. No. 16/317,942 preliminary amendment filed Jan. 15, 2019.
Sangwai & Vavia, "Amorphous ternary cyclodextrin nanocomposites of telmisartan for oral drug delivery: Improved solubility and reduced pharmacokinetic variability," Int. J. Pharmaceutics 453, 423-32, available online Aug. 28, 2012.
Yu et al., "Determination of the equilibrium solubility of tecovirimat and its apparent oil/water partition coefficients using HPLC," Mil. Med. Sci. 36, 49-55, 2012.
International Preliminary Report on Patentability for PCT/CN2017/091650, dated Nov. 12, 2018, 13 pages.
Mennini et al., "Analysis of physicochemical properties of ternary systems of oxaprozin with randomly methylated-?-cyclodextrin and L-arginine aimed to improve the drug solubility," J. Pharm. Biomed. Analy. 129, 350-58, 2016.
Zong et al., U.S. Appl. No. 16/317,942, Advisory Action dated Apr. 16, 2021.
Zhong et al., U.S. Appl. No. 16/317,942, final office action dated Feb. 4, 2021.

* cited by examiner

INJECTABLE PHARMACEUTICAL COMPOSITION OF TECOVIRIMAT AND PREPARATION METHOD THEREOF

TECHNICAL FIELD

The present invention belongs to the technical field of medicine, particularly, relates to a Tecovirimat-containing pharmaceutical composition for injection and a preparation method thereof.

BACKGROUND ART

Smallpox is a highly lethal and infectious disease, which is mainly spread by droplet or clothing, and the clinical manifestations of which are facial and systemic rashes until death. Although WHO declared in 1980 that smallpox had been eliminated in the nature, smallpox will still have disastrous consequences for humans or even cause wars around the world once it is unintentionally or deliberately released. Since smallpox vaccines have serious adverse reactions, medical therapy is still necessary. However, up to now, no therapeutic regimen against smallpox has been approved worldwide.

Tecovirimat (designated as ST-246, with a chemical name of 4-trifluoromethyl-N-(3,3a,4,4a,5,5a,6,6a-octahydro-1,3-dioxo-4,6-ethenocycloprop[f]isoindol-2(1H)-yl)-benzamide, Formula 1) is a highly active small-molecule virus inhibitor, which works by binding to viral genes so as to prevent viral release in a cell. In addition, the use of Tecovirimat and a smallpox vaccine in combination can also prevent and treat the adverse reactions caused by the smallpox vaccine, reduce the damage level and promote wound healing. However, Tecovirimat has a very poor water solubility, which is less than 3 μg/ml, and its low solubility restricts its clinical application.

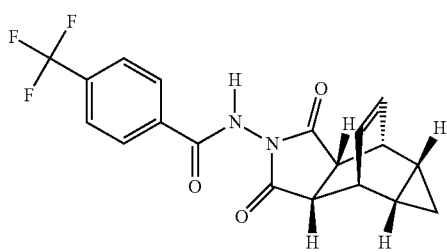

Formula 1

CN201180048043.1 discloses a novel liquid preparation in which Tecovirimat is solubilized in cyclodextrin and a novel method for preparing the preparation. In the method, the solubility of Tecovirimat (ST-246) is increased to 1.5-11 mg/ml by using 20%-40% (w/v) hydroxypropyl-cyclodextrin (HP-β-CD) at 37° C. In particular, Tecovirimat (ST-246) can have a maximal solubility of 21.23 mg/ml by using 40% (w/v) HP-β-CD at 70° C. The presence of a cosolvent (PEG400) and a nonionic surfactant (Tween 80) cannot further improve the solubility of ST-246 in HP-β-CD.

Contents of Invention

After research, the inventors have creatively invented a novel ternary solubilizing composition comprising Tecovirimat, cyclodextrin, and an additive Meglumine (MEG), which greatly improves the solubility (with a maximal solubility of up to 152 mg/ml) of the Tecovirimat with poor solubility as compared with the prior art, and has the advantages such as simple formulation process, short preparation time, stable quality, strong controllability, good reproducibility and low cost.

The present invention includes the following items:

1. A pharmaceutical composition of Tecovirimat for injection, comprising Tecovirimat as an active ingredient, cyclodextrin and an additive,
wherein said additive is selected from the group consisting of meglumine, glycine, arginine, hydroxypropyl methyl cellulose, polyethylene glycol, chitosan, and polyvinyl pyrrolidone, and is preferably meglumine.

2. The pharmaceutical composition according to Item 1 of the present invention, wherein said cyclodextrin is selected from the group consisting of α-cyclodextrin, β-cyclodextrin, γ-cyclodextrin and a pharmaceutically acceptable cyclodextrin derivative (e.g. dimethyl-β-cyclodextrin, 2-hydroxyethyl-β-cyclodextrin, 2-hydroxypropyl-β-cyclodextrin, 3-hydroxypropyl-β-cyclodextrin, trimethyl-β-cyclodextrin);
preferably, said cyclodextrin is selected from the group consisting of β-cyclodextrin, dimethyl-β-cyclodextrin, 2-hydroxyethyl-β-cyclodextrin, 2-hydroxypropyl-β-cyclodextrin, 3-hydroxypropyl-β-cyclodextrin, and trimethyl-β-cyclodextrin;
further preferably, said cyclodextrin is selected from the group consisting of 2-hydroxypropyl-β-cyclodextrin, and 3-hydroxypropyl-β-cyclodextrin;
further more preferably, said cyclodextrin is 2-hydroxypropyl-β-cyclodextrin.

3. The pharmaceutical composition according to Item 1 or Item 2 of the present invention, wherein said cyclodextrin and Tecovirimat have a weight ratio of 4~10:1, preferably 5~8:1, further preferably 5:1, 6:1, 7:1, or 8:1, more preferably 6:1.

4. The pharmaceutical composition according to any one of Items 1 to 3 of the present invention, wherein said additive and Tecovirimat have a weight ratio of 0.5~5:1, preferably 1~4:1, further preferably 1:1, 1.6:1, 2:1, 3:1, or 4:1, more preferably 2:1 or 1.6:1.

5. The pharmaceutical composition according to any one of Items 1 to 4 of the present invention, wherein said additive and cyclodextrin have a weight ratio of 1:1~5, preferably 1: 2~4, further preferably 1:2.5, 1:3, 1:3.5, or 1:3.75.

6. The pharmaceutical composition according to any one of Items 1 to 5 of the present invention, wherein said pharmaceutical composition further comprises one or more components selected from the group consisting of water, glucose, and physiological saline.

7. The pharmaceutical composition according to any one of Items 1 to 6 of the present invention, wherein said pharmaceutical composition is a liquid, wherein Tecovirimat preferably has a concentration of 15~80 mg/ml, more preferably has a concentration of 50 mg/ml.

8. The pharmaceutical composition according to any one of Items 1 to 7 of the present invention, wherein an amount of said hydroxypropyl-β-cyclodextrin is 10% (w/v)~40% (w/v), preferably 30% (w/v).

9. A method for preparing the pharmaceutical composition according to any one of Items 1 to 8 of the present invention, comprising the following steps:
a) dissolving an additive and cyclodextrin in a desired volume of water, and mixingwell;
b) adding Tecovirimat, and stirring well;
c) carrying out sterilization,
optionally, sterilization is followed by drying, to obtain the desired product.

10. The method for preparing the pharmaceutical composition according to Item 9 of the present invention, wherein said drying is freeze-drying.

11. A method for treating smallpox, comprising administering to a subject in need thereof a therapeutically and/or prophylactically effective amount of the pharmaceutical composition according to any one of Items 1 to 8 of the present invention.

12. The pharmaceutical composition according to any one of Items 1 to 8 of the present invention, for use in the treatment of smallpox.

13. Use of the pharmaceutical composition according to any one of Items 1 to 8 of the present invention for the manufacture of a medicament for treating smallpox.

In a preferred embodiment, the pharmaceutical composition according to the present invention can be prepared by the following method comprising:

a. dissolving an additive and cyclodextrin in a desired volume of water, and mixing well;

b. adding the active ingredient Tecovirimat, and stirring in a water bath;

c. subjecting the prepared solution to aseptic filtration or autoclaving;

d. subpackaging the resultant solution into vials or ampoules, which are then sealed/capped.

In another preferred embodiment, the pharmaceutical composition according to the present invention can also be prepared by another method comprising:

a. dissolving an additive and cyclodextrin in a desired volume of water, and mixing well;

b. adding the active ingredient Tecovirimat, and stirring in a water bath;

c. subjecting the prepared solution to freeze-drying to remove water;

d. subpackaging the resultant solution into vials or ampoules, which are then sealed/capped.

In the present invention, the term "an additive" refers to a substance that can interact with an active ingredient, so as to enhance the inclusion efficiency of cyclodextrin, and further to improve drug solubility.

In the present invention, "% (w/v)" refers to a mass/volume concentration, which represents the mass (expressed as gram) of a solute contained in per 100 ml of a solution. For example, 20% (w/v) represents 20 g of a solute contained in per 100 ml of a solution.

DESCRIPTION OF THE DRAWINGS

FIG. 1 shows the solubility curves of Tecovirimat in different solutions at 25° C., 37° C. and 60° C., wherein:

FIG. 1(A) shows the solubility curve of Tecovirimat in a solution containing 2-hydroxypropyl-β-cyclodextrin alone;

SPECIFIC MODES FOR CARRYING OUT THE INVENTION

Figure 1:
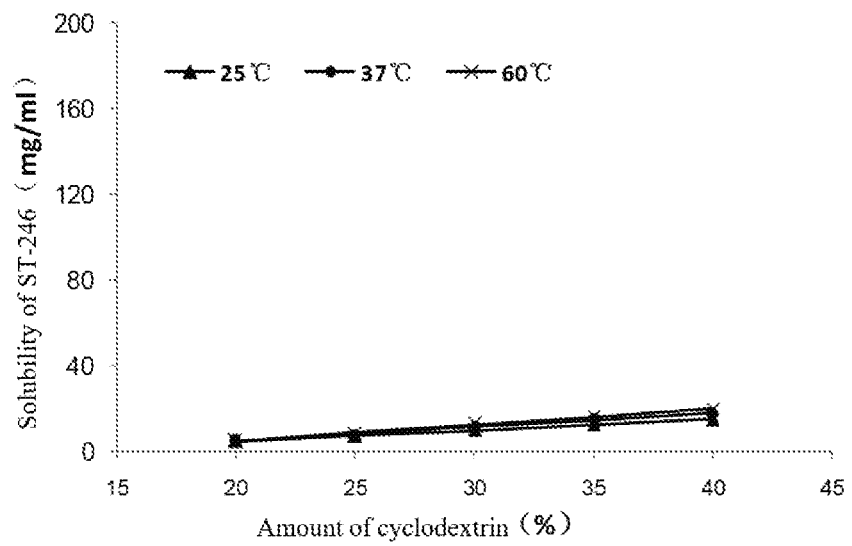
Figure 1B:
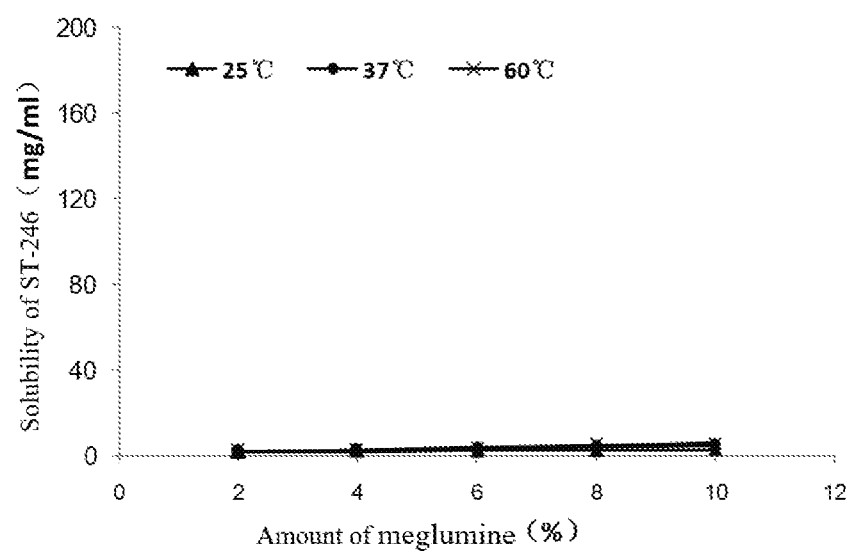
FIG. 1(B) shows the solubility curve of Tecovirimat in a solution containing meglumine alone.
Figure 1C:
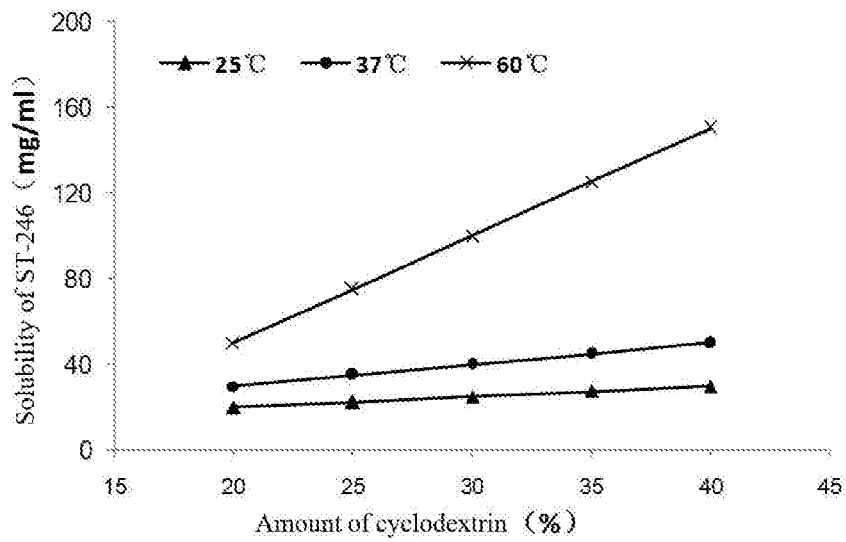
FIG. 1(C) shows the solubility curve of Tecovirimat in a solution containing both 2-hydroxypropyl-β-cyclodextrin and meglumine (the amount of meglumine is 5%).

The embodiments of the present invention are described in detail by combining the following examples. However, a person skilled in the art will understand that the following examples and experimental examples are only used to describe the present invention, and should not be regarded as defining the scope of the present invention. In the case where the concrete conditions are not indicated in the examples and experimental examples, the examples are carried out according to conventional conditions or the conditions recommended by manufacturers. The reagents or apparatuses, the manufacturers of which are not indicated, are the conventional products that are commercially available.

Example 1: Preparation of a Solubilizing Composition Comprising Tecovirimat and Meglumine for Injection

TABLE 1

| Formulation | | |
| --- | --- | --- |
| Name of raw material | Amount of raw material (g/100 ml) | Description of the Formulation |
| Tecovirimat | 5.0 | The concentration of the active ingredient is 50 mg/ml |
| meglumine | 10.0 | The amount of the additive is 10% (w/v) |
| hydroxypropyl-β-cyclodextrin | 30.0 | The amount of cyclodextrin is 30% (w/v) |
| water | adding to 100 ml | — |

Preparation method: a prescribed amount of meglumine and hydroxypropyl-β-cyclodextrin were dissolved in a certain volume of water, and then a prescribed amount of Tecovirimat was added; water was added to a final volume of 100 ml, and the resultant mixture was stirred at a medium speed at 60° C. in a water bath, thereby obtaining the desired composition.

Example 2: Preparation of a Solubilizing Composition Comprising Meglumine and Tecovirimat for Injection

TABLE 2

| Formulation | | |
| --- | --- | --- |
| Name of raw material | Amount of raw material (g/100 ml) | Description of the Formulation |
| Tecovirimat | 5.0 | The concentration of the active ingredient is 50 mg/ml |
| meglumine | 8.0 | The amount of the additive is 8% (w/v) |
| hydroxypropyl-β-cyclodextrin | 30.0 | The amount of cyclodextrin is 30% (w/v) |
| water | adding to 100 ml | — |

Preparation method: a prescribed amount of meglumine and hydroxypropyl-3-cyclodextrin were dissolved in a certain volume of water, and then a prescribed amount of Tecovirimat was added; water was added to a final volume of 100 ml, and the resultant mixture was stirred at a medium speed at 60° C. in a water bath, thereby obtaining the desired composition.

Experimental Example 1: Experiment on Compatible Stability of a Solubilizing Composition of Tecovirimat for Injection Experimental method: the solubilizing composition for injection (4 ml) as prepared in Example 1 was added to 100 ml glucose injection or physiological saline, and changes of the appearance, pH value, and the related substance were observed at 0 h, 2 h, 4 h, 6 h, and 8 h, respectively.

The experimental results were shown in Table 3 and Table 4.

TABLE 3

Experimental result on stability when the solubilizing composition is compatible with glucose injection

| Time | Appearance | pH value | Maximal single impurity % | Total impurity % |
|---|---|---|---|---|
| 0 h | clear, no particles visible to the human eye | 9.81 | 0.053 | 0.123 |
| 2 h | clear, no particles visible to the human eye | 9.82 | 0.051 | 0.125 |
| 4 h | clear, no particles visible to the human eye | 9.81 | 0.048 | 0.122 |
| 6 h | clear, no particles visible to the human eye | 9.75 | 0.048 | 0.120 |
| 8 h | clear, no particles visible to the human eye | 9.79 | 0.051 | 0.119 |

TABLE 4

Experimental result on stability when the solubilizing composition is compatible with physiological saline

| Time | Appearance | pH value | Maximal single impurity % | Total impurity % |
|---|---|---|---|---|
| 0 h | clear, no particles visible to the human eye | 9.96 | 0.048 | 0.119 |
| 2 h | clear, no particles visible to the human eye | 9.95 | 0.048 | 0.123 |
| 4 h | clear, no particles visible to the human eye | 9.95 | 0.045 | 0.122 |
| 6 h | clear, no particles visible to the human eye | 9.95 | 0.050 | 0.121 |
| 8 h | clear, no particles visible to the human eye | 10.00 | 0.050 | 0.118 |

The experimental results show that the solubilizing composition had good compatibility with glucose injection or physiological saline.

Experimental Example 2: Experiment on Dilution Stability of a Solubilizing Composition of Tecovirimat for Injection Experimental method: to 10 test tubes, designated as 1~10, 1 ml phosphate buffer (pH 7.4) was added, and to Tube 1, the solubilizing composition (1 ml) as prepared in Example 1 or Example 2 was then added; the resultant solution was mixed well under shaking, the resultant solution (1 ml) was taken from Tube 1, and added to Tube 2; the operation was repeated until Tube 10, and the tubes were on standing and were observed for clarity.

Experimental result: no drug was precipitated in 10 tubes within 5 min, indicating that the formulation had good compatibility with the phosphate buffer (pH=7.4).

Experimental Example 3: Solubility Test

An excessive amount of Tecovirimat was added to an aqueous solution comprising meglumine and cyclodextrin at a different ratio to form a suspension. The suspension was placed in a constant-temperature incubation shaker, and was shaken at a temperature of 25±1° C., 37±1° C. and 60±1° C. for 72 h, respectively. After reaching equilibrium, the suspension was filtered through a 0.45 μm hydrophilic filter membrane to obtain a filtrate. After the filtrate was properly diluted with an acetonitrile-water (50:50, v/v) solution, the absorbance was measured at 224 nm, and the solubility of Tecovirimat was calculated. The corresponding solubility curve was plotted by using the solubility of the drug as the ordinate, and using the concentration of cyclodextrin and/or meglumine as the abscissa. The solubility curves of Tecovirimat at 25° C., 37° C. and 60° C. were shown in FIG. 1(A) to FIG. 1(C).

As seen from FIG. 1(A), the solubility of Tecovirimat in water increased linearly with the increase in the amount of cyclodextrin. The amount of cyclodextrin was in the range from 20% (w/v) to 40% (w/v), and the solubility of Tecovirimat in water at 25° C., 37° C. and 60° C. was 5 mg/ml to 15 mg/ml, 5 mg/ml to 18 mg/ml, and 5 mg/ml to 20 mg/ml, respectively.

As seen from FIG. 1(B): the solubility of Tecovirimat in water also increased linearly with the increase in the amount of meglumine. The amount of meglumine was in a range from 2% (w/v) to 10% (w/v), and the solubility of Tecovirimat in water at 25° C., 37° C. and 60° C. was 2 mg/ml to 7 mg/ml, 2 mg/ml to 9 mg/ml, and 2 mg/ml to 10 mg/ml, respectively.

As seen from FIG. 1(C): the use of cyclodextrin and meglumine in combination could significantly increase the solubility of Tecovirimat in water. When the amount of meglumine was 10% (w/v) and the amount of cyclodextrin was in a range from 20% (w/v) to 40% (w/v), the solubility of Tecovirimat in water at 25° C., 37° C. and 60° C. was 20 mg/ml to 80 mg/ml, 30 mg/ml to 100 mg/ml, and 50 mg/ml to 150 mg/ml, respectively. This indicated that meglumine and cyclodextrin had an unexpected synergistic effect on solubilization of Tecovirimat.

According to the experimental result of solubility, when the amount of cyclodextrin was in a range from 5% to 40% (w/v), the thermodynamic parameters were calculated for the inclusion complex formed by the drug and cyclodextrin. The result was shown in Table 5. A negative $\Delta G$ indicated that inclusion process could occur spontaneously; a positive $\Delta H$ indicated that the main driving force of inclusion process was hydrophobic interaction, and meanwhile the inclusion process was an endothermic reaction, and the inclusion reaction could be promoted by increasing the temperature properly. However, the ternary composition had a lower $\Delta H$ value because the entrance of meglumine into the cavity resulted in the release of more enthalpy-rich water. A positive $\Delta S$ indicated that the inclusion process was an enthalpy increasing process, and the ternary composition had a lower $\Delta S$ value because the degree of freedom for Tecovirimat and meglumine in the cavity was reduced, and a more stable inclusion system was formed.

TABLE 5

Thermodynamic parameters of different solubilizing compositions

| Components of a solution | Drug concentration (mg/ml) | Amount of MEG % (w/v) | ΔG (KJ/mol) 25° C. | ΔG (KJ/mol) 37° C. | ΔG (KJ/mol) 60° C. | ΔH (KJ/mol) | ΔS (J/mol K) |
|---|---|---|---|---|---|---|---|
| Tecovirimat/cyclodextrin | 5~20 | 0 | −8.782 | −9.610 | −11.197 | 11.780 | 0.069 |
| Tecovirimat/cyclodextrin/ 0.25% meglumine | 6~24 | 0.25% (w/v) | −6.712 | −7.420 | −8.777 | 10.870 | 0.059 |
| Tecovirimat/cyclodextrin/ 1% meglumine | 7~26 | 1.0% (w/v) | −4.614 | −5.190 | −6.294 | 9.690 | 0.048 |

Note:
among the components of the solution, the amount of cyclodextrin was 5%~40% (w/v)

Experimental Example 4: Nuclear Magnetic Resonance (NMR) Spectroscopic Assay

Experimental method: a suitable amount of Tecovirimat, meglumine, cyclodextrin, a binary composition (Tecovirimat/meglumine at a weight ratio of 1:2), a binary composition of (Tecovirimat/cyclodextrin at a weight ratio of 1:6), and a ternary composition (Tecovirimat/meglumine/cyclodextrin at a weight ratio of 1:2:6) were dissolved in DMSO-d6 to prepare samples, respectively, and the possible intermolecular interaction was analyzed by $^1$H NMR spectroscopy.

Figure 2:
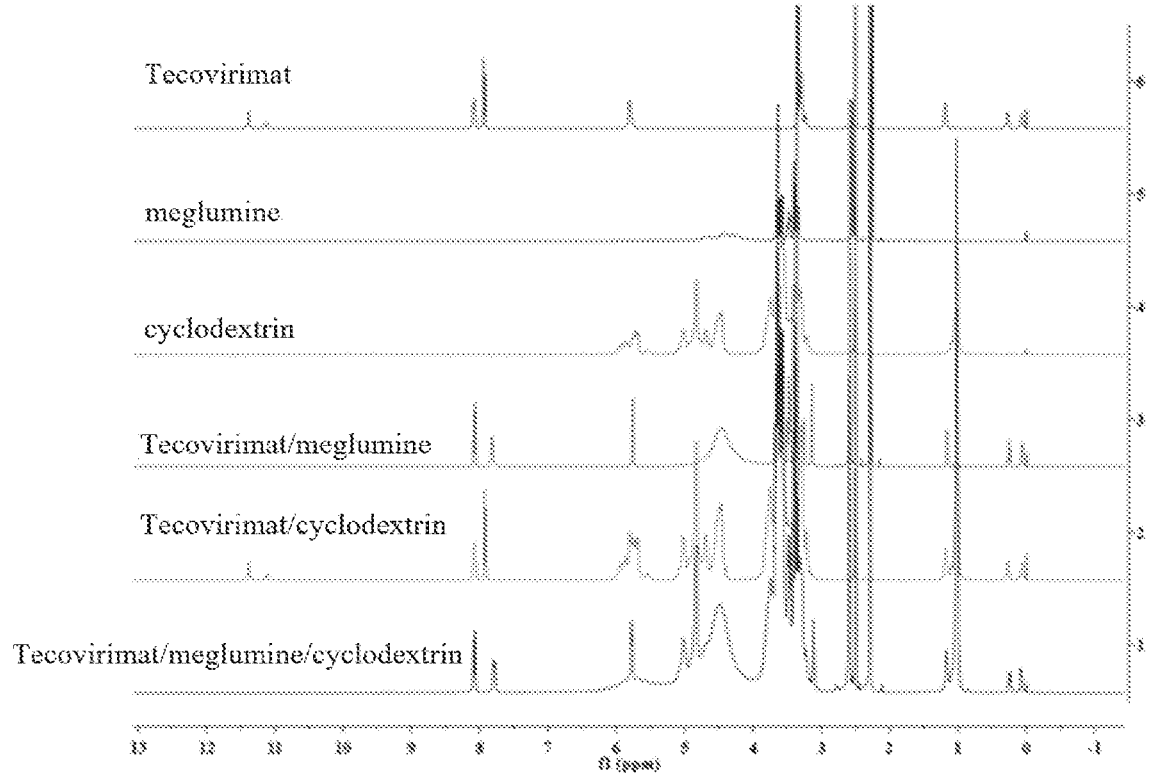
FIG. 2 shows $^1$H Nuclear Magnetic Resonance (NMR) spectra of Tecovirimat, meglumine, cyclodextrin, binary compositions (Tecovirimat/meglumine, Tecovirimat/cyclodextrin), and a ternary composition (Tecovirimat/meglumine/cyclodextrin).

Experimental result: the NMR spectra were shown in FIG. 2, and it was deduced by chemical shift results that hydrogen bonds were formed between Tecovirimat and meglumine, the presence of meglumine changed the steric structure of Tecovirimat, when the drug Tecovirimat entered the cavity of cyclodextrin, electrostatic interaction occurred between Tecovirimat and cyclodextrin. Therefore, the solubilization of Tecovirimat was resulted from the interactions of the components in the ternary composition, in which hydrogen bonding and inclusion played a major role.

To sum up, as compared with the prior art, the present invention provides a pharmaceutical composition of Tecovirimat; the addition of an additive makes the drug to be included more easily, which greatly enhance the inclusion efficiency of cyclodextrin and simplifies the operation; and meanwhile, the amount of cyclodextrin used is reduced, thereby reducing the potential medicament risk. The pharmaceutical composition also has the advantages such as simple formulation, low cost, easy operation, stable and controllable quality, and good reproducibility.

The invention claimed is:

1. A pharmaceutical composition of Tecovirimat for injection, comprising Tecovirimat as an active ingredient, a cyclodextrin and an additive, wherein said additive is meglumine.

2. The pharmaceutical composition according to claim 1, wherein said cyclodextrin is selected from the group consisting of α-cyclodextrin, β-cyclodextrin, γ-cyclodextrin, a hydroxypropyl-β-cyclodextrin, dimethyl-β-cyclodextrin, 2-hydroxyethyl-β-cyclodextrin, and trimethyl-β-cyclodextrin.

3. The pharmaceutical composition according to claim 1, wherein said cyclodextrin and Tecovirimat have a weight ratio of 4-10:1.

4. The pharmaceutical composition according to claim 1, wherein said additive and Tecovirimat have a weight ratio of 0.5-5:1.

5. The pharmaceutical composition according to claim 1, wherein said additive and cyclodextrin have a weight ratio of 1:1-5.

6. The pharmaceutical composition according to claim 1, wherein said pharmaceutical composition further comprises one or more components selected from the group consisting of water, glucose, and physiological saline.

7. The pharmaceutical composition according to claim 1, wherein said pharmaceutical composition is a liquid.

8. The pharmaceutical composition according to claim 2, wherein said cyclodextrin is the hydroxypropyl-β-cyclodextrin, and wherein an amount of said hydroxypropyl-β-cyclodextrin is 10% (w/v)-40% (w/v).

9. The pharmaceutical composition according to claim 2, wherein said cyclodextrin is selected from the group consisting of dimethyl-β-cyclodextrin, 2-hydroxyethyl-β-cyclodextrin, 2-hydroxypropyl-β-cyclodextrin, 3-hydroxypropyl-β-cyclodextrin, and trimethyl-β-cyclodextrin.

10. The pharmaceutical composition according to claim 2, wherein said cyclodextrin is selected from the group consisting of β-cyclodextrin, dimethyl-β-cyclodextrin, 2-hydroxyethyl-β-cyclodextrin, 2-hydroxypropyl-β-cyclodextrin, 3-hydroxypropyl-β-cyclodextrin, and trimethyl-β-cyclodextrin.

11. The pharmaceutical composition according to claim 2, wherein said cyclodextrin is the hydroxypropyl-β-cyclodextrin, wherein the hydroxypropyl-β-cyclodextrin is selected from the group consisting of 2-hydroxypropyl-β-cyclodextrin and 3-hydroxypropyl-β-cyclodextrin.

12. The pharmaceutical composition according to claim 11, wherein said cyclodextrin is 2-hydroxypropyl-β-cyclodextrin.

13. The pharmaceutical composition according to claim 3, wherein said cyclodextrin and Tecovirimat have a weight ratio of 5-8:1.

14. The pharmaceutical composition according to claim 4, wherein said additive and Tecovirimat have a weight ratio of 1-4:1.

15. The pharmaceutical composition according to claim 5, wherein said additive and cyclodextrin have a weight ratio of 1:2-4.

16. The pharmaceutical composition according to claim 7, wherein Tecovirimat has a concentration of 15-80 mg/ml.

17. A method for preparing the pharmaceutical composition according to claim 1, comprising the following steps:
   a) dissolving an additive and cyclodextrin in a desired volume of water, and mixing well, wherein the additive is meglumine;
   b) adding Tecovirimat, and stirring well; and
   c) carrying out sterilization.

18. The method for preparing the pharmaceutical composition according to claim 17, wherein said drying is freeze-drying.

19. A method for treating smallpox, comprising administering to a subject in need thereof a therapeutically and/or prophylactically effective amount of the pharmaceutical composition according to claim 1.

\* \* \* \* \*